United States Patent [19]

Zissimopoulos et al.

[11] 4,312,341
[45] Jan. 26, 1982

[54] BUBBLE DETECTOR

[75] Inventors: Nick Zissimopoulos, Schaumburg; John Baron, Wheeling, both of Ill.

[73] Assignee: Baxter Travenol Laboratories, Inc., Deerfield, Ill.

[21] Appl. No.: 103,040

[22] Filed: Dec. 13, 1979

[51] Int. Cl.³ .............................................. A61M 5/16
[52] U.S. Cl. ...................... 128/214 E; 128/DIG. 13; 356/440; 356/410; 356/40
[58] Field of Search ................ 128/DIG. 13, 214 E, 128/214 C; 356/440, 410, 40; 222/159, 450; 138/103

[56] References Cited

U.S. PATENT DOCUMENTS

| | | | |
|---|---|---|---|
| 3,163,176 | 12/1964 | Darling | 128/214 E |
| 3,172,502 | 3/1965 | Wells | 138/103 |
| 3,527,542 | 9/1970 | Penhasi et al. | 356/40 |
| 4,038,982 | 8/1977 | Burke et al. | 128/214 E |
| 4,144,144 | 9/1978 | Hyman | 340/632 |

FOREIGN PATENT DOCUMENTS 2601432  7/1977  Fed. Rep. of Germany ... 128/214 E

Primary Examiner—Robert W. Michell
Assistant Examiner—Nancy A. B. Swisher
Attorney, Agent, or Firm—Paul C. Flattery; John P. Kirby, Jr.; Eugene M. Cummings

[57] ABSTRACT

In a flow metering apparatus a bubble detector for detecting bubble formation in tubing subject to deformation from internal fluid pressure includes a light source and a light detector. The light detector is positioned on the opposite side of the tubing from the light source such that the light transmitted through the tubing to the detector is dependent on the presence of fluid in the tubing and on the shape of the lumen of the tubing. A control circuit responsive to the output of the detector interrupts operation of the metering apparatus when the light transmitted through the tubing falls below a predetermined minimum level. False interruptions resulting from deformation of the tubing by pressure changes in the fluid are prevented by forming members which engage the wall of the tubing adjacent the light source and light detector.

8 Claims, 12 Drawing Figures

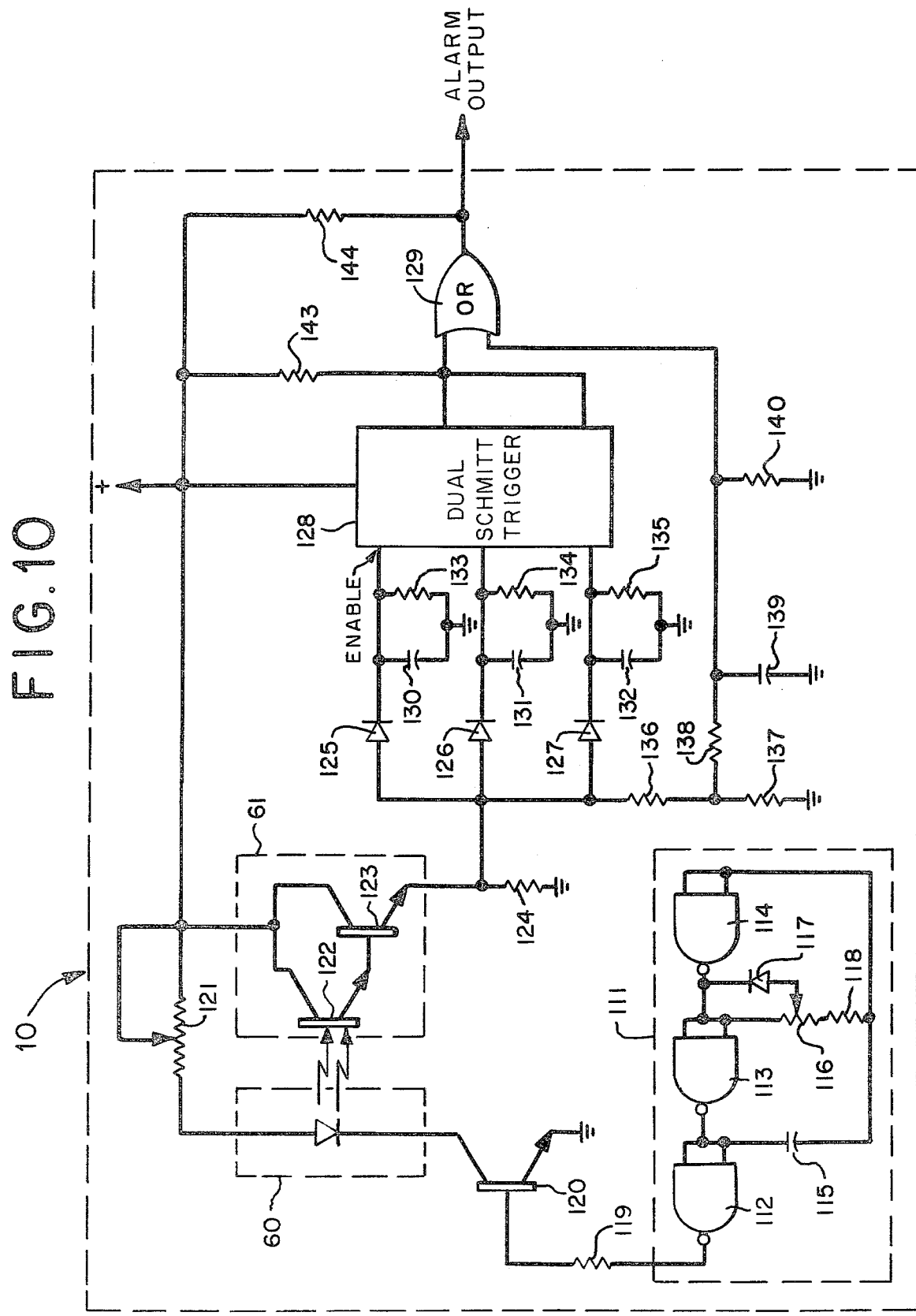

BUBBLE DETECTOR

BACKGROUND OF THE INVENTION

The present invention relates generally to fluid infusion systems, and more particularly to an improved apparatus for detecting the formation of bubbles in such systems.

The infusing of fluids such as parenteral fluids and blood into the human body is usually accomplished by means of an administration set and metering apparatus which controls the rate of flow of fluid through the set. Peristaltic-type pumps, which function by repetitively compressing and expanding a section of tubing, have proven particularly attractive for use in such metering apparatus since they do not introduce the possibility of leakage or contamination into the system, while providing positive control of fluid flow through the system. One form of metering apparatus employing a peristaltic-type pump is described in U.S. Pat. No. 4,155,362, which issued to Thurman S. Jess on May 21, 1979, and is assigned to the present assignee. A successful commercial embodiment of this apparatus is currently marketed as the Travenol Model 2M014 infusion pump by Baxter Travenol Laboratories, Inc., of Deerfield, Illinois.

One problem which arises with the use of liquid infusion sets is that dissolved gases in the liquid being infused may be released as bubbles as the liquid is subjected to pressure and/or temperature changes as it passes through the pump of the metering apparatus. These bubbles may coalesce and form larger bubbles or pockets of gas which may be infused along with the liquid into the body, an occurence which may be harmful or even fatal to the patient under certain circumstances.

To prevent gas from being infused it has become common practice to locate a bubble detector downline of the metering apparatus pump to automatically stop the apparatus should gas bubbles be detected. Such sensors typically employ a light source and a light detector positioned on opposite sides of the administration set tubing to monitor the level of light transmitted through the tubing. Operation of the metering apparatus is interrupted and an alarm is sounded when the transmitted light level falls below a predetermined level. To this end, the lens effect of the fluid in the lumen of the tubing may be employed to enhance the difference in transmission levels between fluid and no fluid conditions.

One problem encountered with such bubble detectors is that fluid pressure changes in the tubing of the administration set such as may result from the use of a downline flow restriction, as in the Travenol Model 2M8014 infusion pump may deform the wall of the tubing from its unstressed shape and diminish the lens effect. This has the potential of diminishing the reliability and sensitivity of the bubble detector. The present invention is directed to a bubble detector which is not subject to such variations in effectiveness as a result of changes in fluid pressure.

Accordingly, it is a general object of the present invention to provide a new and improved bubble detector.

It is another object of the present invention to provide a new and improved bubble detector wherein means are provided for preventing deformation of the tubing wall as a result of internal fluid pressure.

It is a further object of the present invention to provide a new and improved bubble detector suitable for use with vinyl tubing or the like subject to deformation from internal fluid pressure.

SUMMARY OF THE INVENTION

The invention is directed to a flow metering apparatus for controlling the flow of fluids through an administration set of the type having transparent tubing subject to deformation from internal fluid pressure. The apparatus includes a bubble detector comprising a light source arranged at one side of the tubing, and a light detector generally arranged at the opposite side of the tubing opposite the light source and defining a light path through the tubing. The detector generates an output signal in response to the intensity of light from the light source transmitted through the tubing, the intensity of the transmitted light being dependent on the presence of fluid within the lumen of the tubing and on the shape of the lumen between the source and the detector. Control circuit means responsive to the output signal are provided for interrupting operation of the flow metering apparatus upon the intensity of the transmitted light falling below a predetermined minimum level. Platen means including at least one forming member engaging the tubing about a substantial portion of its circumference adjacent the light path are provided for preventing deformation of the tubing and consequent changes in the intensity of the transmitted light with fluid pressure changes in the lumen of the tubing.

The invention is further directed to a flow system for infusing fluid from a reservoir into the human body. The system comprises a length of transparent tubing subject to deformation from internal fluid pressure. Metering means operatively engaging the tubing are provided for urging fluid through the tubing at a predetermined rate. The system further includes a light source arranged at one side of the tubing downline of the metering means, and a light detector generally arranged at the opposite side of the tubing opposite the light source and defining a light path through the tubing, the detector generating an output signal in response to the intensity of light from the light source transmitted through the tubing, the intensity of the transmitted light being dependent on the presence of fluid within the lumen of the tubing and on the shape of the lumen between the source and the detector. Control circuit means responsive to the output signal are provided for interrupting operation of the metering means upon the intensity of the transmitted light falling below a predetermined minimum level. Platen means including at least one forming member engaging the tubing about a substantial proportion of the circumference of the tubing adjacent the light path are provided for preventing deformation of the tubing and consequent changes in the intensity of the transmitted light with fluid pressure changes in the lumen of the tubing.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, and the several figures of which like reference numerals identify like elements, and in which:

FIG. 10 is a simplified schematic diagram of a preferred detector circuit for use in conjunction with the bubble detector of the invention.

DESCRIPTION OF THE PREFERRED EMBODIMENT

Figure 1:
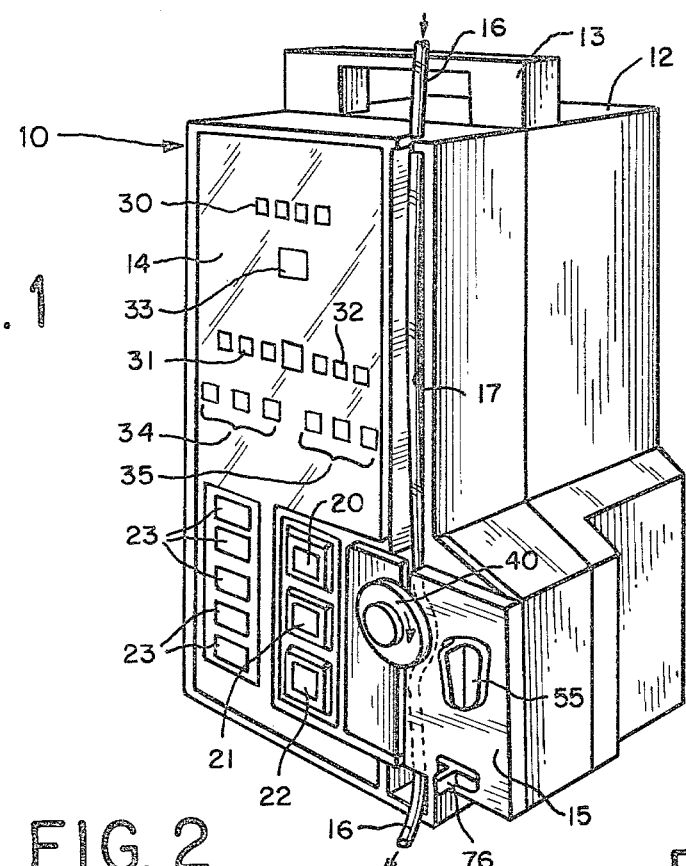
FIG. 1 is a perspective view of a metering apparatus incorporating a bubble detector constructed in accordance with the invention.

Referring to the figures, and particularly to FIG. 1, a peristaltic-type flow metering apparatus 10 for use in conjunction with an administration set for controlling the flow of fluid into a vein or artery includes a generally rectangular housing 12 having a handle 13 at one end thereof for convenient carrying. The front surface of the housing includes a control panel 14 which allows the operator to control and monitor the operation of the metering apparatus, and a peristaltic-type flow metering head 15 for compressing a section of tubing 16 of the administration set to effect control of fluid flow therein. A channel 17 is provided above the metering head 15 for maintaining a portion of the tubing segment in convenient view of the operator whereby flow irregularities can be more readily observed.

The administration set, of which tubing segment 16 is a part, and which may be conventional in design and construction, is preferably formed of a plastic material such as vinyl and packaged in a sterile and non-pyrogenic condition. To avoid the danger of contamination, the administration set is normally utilized for one application only, and is disposed of after a single use.

The operating mode of metering apparatus 10 is controlled by means of a push button STOP switch 20, a push button START switch 21, and a push button power ON-OFF switch 22. Each of these push button switches includes an internal indicator lamp which provides a positive indication of the operation of the operating mode of the apparatus. Various abnormal operating conditions are annunciated by means of indicator lights 23 contained on the control panel to the left (as viewed in FIG. 1) of the mode control push buttons.

Control panel 14 further includes a digital display 30 of volume infused, a digital display 31 of volume to be infused, and a digital display 32 of the fluid flow rate. The volume displayed by display 30 is the volume of fluid actually infused, and can be reset to zero by the operator by means of a push button RESET switch 33. The volume to be infused by display 31 is preset by the operator by means of a set of push button switches 34 to indicate a desired volume of fluid to be infused. Similarly, the infusion rate display 32 is preset by the operator by means of a second set of push button switches 35 to indicate the rate at which infusion is to take place.

The operation of the various indicators, control switches and other features of metering apparatus 10 is described in detail in the copending applications of Thurman S. Jess and Norm Shim, Ser. No. 856,863; Norm Shim, Ser. No. 857,018; Norm Shim and Vincent L. Knigge, Ser. No. 856,927; and Thurman S. Jess, Ser. No. 856,926; all filed Dec. 2, 1977.

Figure 2:
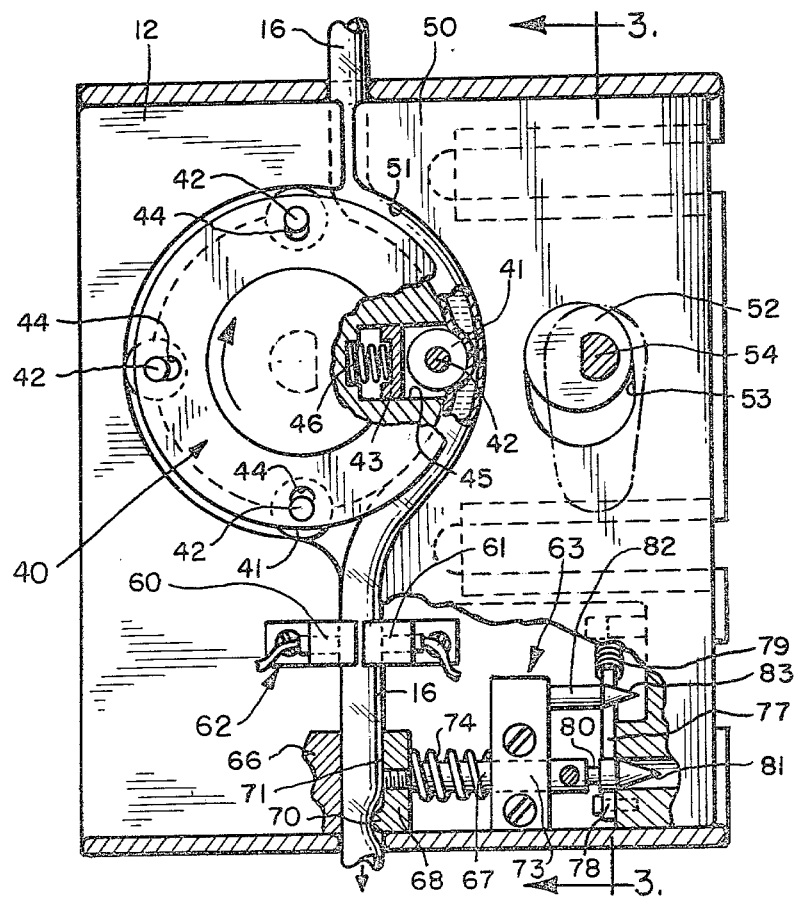
FIG. 2 is an enlarged front elevational view of the metering station of the flow metering apparatus partially in section and partially broken away to illustrate the operation thereof.
Figure 3:
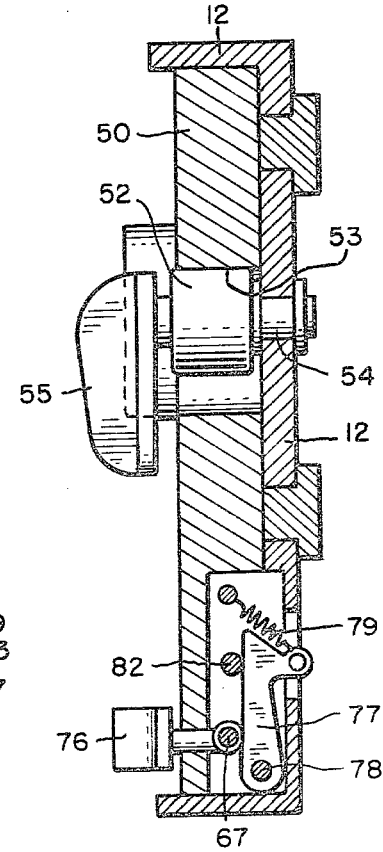
FIG. 3 is a cross-sectional veiw of the metering station taken along line 3—3 of FIG. 2.

Referring to FIGS. 2 and 3, the peristaltic metering head 15 includes a rotor 40 having four pressure rollers 41 disposed in equi-spaced relation about its circumference. The rollers are each mounted on a shaft 42 for free rotation, and the shafts are carried on carriages 43 and constrained to radial movement by respective radial slots 44. Each carriage is mounted for reciprocation within a radial recess 45 and spring loaded radially outward by a helical spring 46 disposed within the recess.

The pump also includes a pressure plate 50 having an arcuate working surface 51 which substantially corresponds in shape to the circumference of rotor 40. The working surface brings tubing 16 into compressive engagement with rollers 41 around at least a portion of the rotor circumference corresponding to the spacing between adjacent rollers. The pressure plate may be reciprocated toward and away from rotor 40 to facilitate installation and removal of tubing 16 by rotation of an eccentric cam 52, which is constrained to operate within a vertical slot 53 provided on the pressure plate. Rotation of the cam is accomplished by a shaft 54 and a user-actuable lever 55 operatively connected to the cam. When the lever 55 is in its vertical position, as shown in FIG. 3, the pressure plate is moved sufficiently close to the rotor circumference to cause tubing 16 to be completely occluded by one of the pressure rollers 41.

After passing through metering station 15, tubing 16 extends between a light source 60 and a photodetector 61, which together comprise a bubble detector head 62. This head, combined with asssociated control circuitry forms a bubble detector system which discontinues operation of the metering apparatus and alerts the operator upon formation of a bubble in the tubing.

The tubing next passes through a flow restriction station 63. This station includes a pressure block 66 and a slidably mounted plunger 67 biased against the sidewall of tubing segment 16. The end of plunger 67 which engages the tubing segment includes a generally L-shaped head portion 68 having a wedge-shaped working surface 70 which occludes the tubing and a generally flat control surface 71 which responds to fluid pressure changes. Plunger 67 is slidably received within a mounting block 73, and extends through the center of a helical compression spring 74 which biases head 68 into engagement with the tubing. The occlusion of the tubing by the flow restriction station increases the pressure of the fluid in the tubing at the point of engagement of the rollers 41 of rotor 40 to assist in restoration of the tubing following compression by the pressure rollers for improved metering accuracy.

Plunger 67 can be opened to facilitate loading or unloading of tubing 16 by means of a lever 76. The plunger is locked open by means of a latch member 77 which is pivotally mounted at 78 to pressure plate 50 and biased by a helical spring 79 for operation within a plane perpendicular to the plunger. Latch member 77 is received in a slot 80 on the plunger when the plunger is moved to its full open position.

To insure that plunger 67 will be released when pressure plate 50 is subsequently closed, an actuator pin 82 having a tapered end surface displaces latch member 77 from slot 80 when the pressure plate is returned to its closed position by rotation of knob 55. This prevents inadvertent operation of the system without the back pressure and gravity flow protection provided by the plunger. Also, when the pressure plate is opened, the displacement of latching member 77 prevents the plunger from being latched open.

Figure 4:
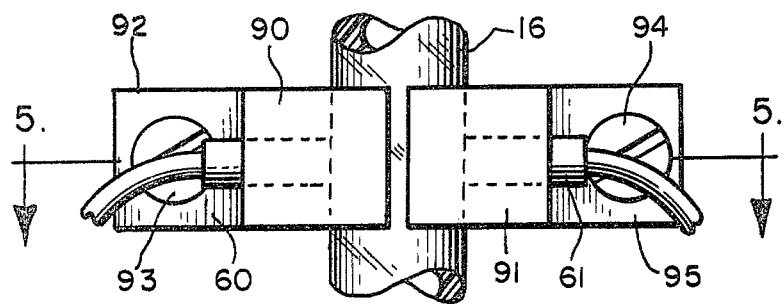
FIG. 4 is an elongated front elevational view of the bubble detector head of the metering station.

In accordance with the invention, metering apparatus 10 includes a bubble detector head 62 which renders the bubble detector system of the apparatus immune to variations in fluid pressure in tubing 16. Referring to FIG. 4, the bubble detector head is seen to comprise first and second forming members 90 and 91 disposed on opposite sides of tubing 16. The first form member 90 is secured to housing 12 by a bolt 93, extending through a flange portion 92. Similarly, the second form member 91 is secured to the slidable pressure plate 50 by means of a bolt 94 extending through a flange portion 95 of the base member.

To provide mounting means for light source 60, the first form member 90 is provided with a bore 96 perpendicularly aligned to the axis of tubing 16. To provide a receptacle for photodetector 61, form member 91 is similarly provided with a perpendicularly aligned bore 97. Bores 96 and 97 are each dimensioned with an inside diameter just slightly larger than the outside diameter of light source 96 and photodetector 97, respectively, to provide a fit for these elements sufficiently tight to maintain the elements in alignment.

Figure 5:
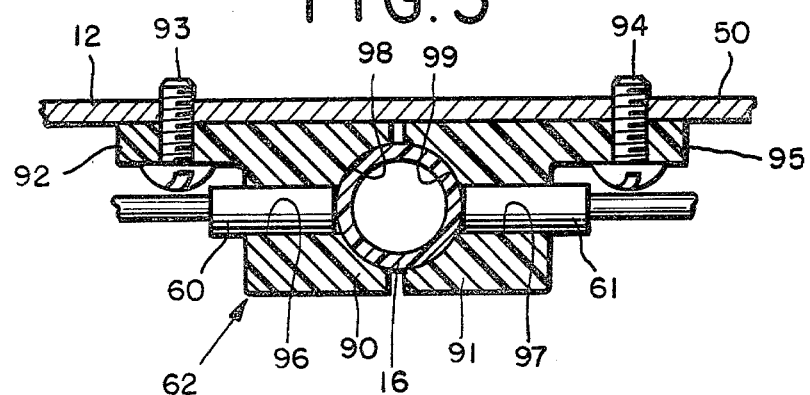
FIG. 5 is a cross-sectional view of the bubble detector head taken along line 5—5 of FIG. 4.

It will be noted that form members 90 and 91 define inwardly concave mandrel surfaces 98 and 99, respectively, between which tubing 16 is held when the form elements 90 and 91 are in their closed position, as shown in FIGS. 4 and 5. The curvature of these mandrel surfaces is dimensioned to correspond closely to the natural or unstressed curvature of the outside surface of tubing 16 so that when the tubing is engaged to the form members the tubing lumen is maintained in its unstressed cross-sectional shape notwithstanding pressure changes in the fluid contained therein.

Figure 6:
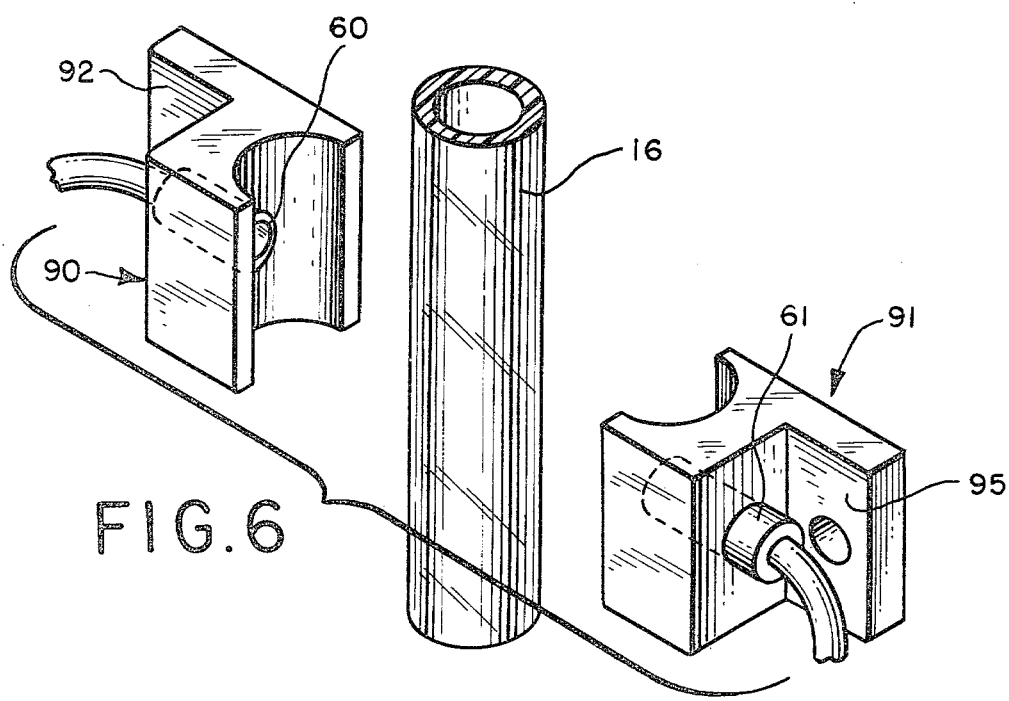
FIG. 6 is an exploded perspective view of the bubble detector head showing the principal components thereof.

To remove the tubing, it is merely necessary to separate form members 90 and 91, as shown in FIG. 6. In metering apparatus 10, this is accomplished automatically upon the operator actuating knob 55 to open metering station 15, since form member 90 is mounted to a stationary housing member, and form member 91 is mounted to the movable pressure plate 50.

Figure 7A:
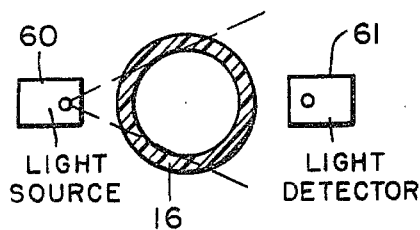
FIG. 7(A) is a diagramatic depiction of the bubble detector head useful in depicting operation of the bubble detector in the absence of fluid.
Figure 7B:
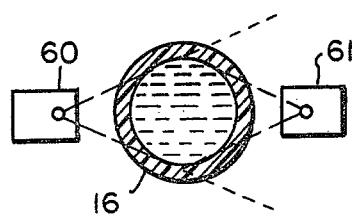
FIG. 7(B) is a diagramatic depiction similar to FIG. 7(A) showing operation of the bubble detector with fluid present.

To illustrate the benefit of maintaining the cross-section of tubing 16 constant, reference is made to FIGS. 7(A) and 7(B) which illustrate the lens effect upon which the detector depends. In FIG. 7(A) no fluid is present in the lumen of tubing 16, and light from light source 60 diverges as it passes through the transparent walls of the tubing. As a result, only a small portion of the light transmitted through the tubing actually falls upon light detector 61, and the resulting signal produced by that device is small. In contrast, when liquid is present in the lumen of the tubing as shown in FIG. 7(B), the circular cross-section of the fluid mass, as defined by the inner surface of the wall of tubing 16, forms a lens which focuses the light on detector 61. As a result, a greater portion of the transmitted light is actually incident on the detector and the resulting detector output signal is stronger. By comparing the light detector output signals for the conditions shown in FIGS. 7(A) and 7(B), appropriate bubble detector circuitry within metering apparatus 10 determines the presence or absence of fluid in the tubing.

Figure 8A:
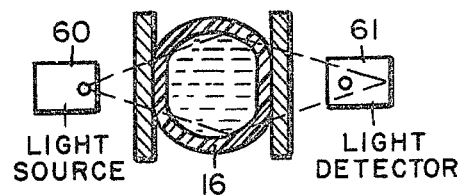
FIG. 8(A) is a simplified diagramatic depiction of a prior art bubble detector head illustrating the effect of deformation of the tubing wall on the operation of the bubble detector.

Referring to FIG. 8(A), in prior art bubble detectors no provision was made for maintaining the tubing in constant cross-section. As a result, as the pressure of the fluid in the tubing lumen increased the walls of the tubing became deformed. This caused the light from light source 60 to be only partially focused on light detector 61, so that the output signal developed by that device was weaker than the signal would have been had the distortion not taken place. As a result, the capability of the bubble detector to distinguish between liquid and no liquid conditions was diminished.

Figure 8B:
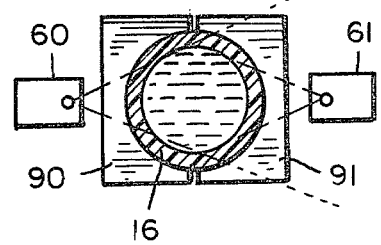
FIG. 8(B) is a simplified diagramatic depiction of the flow detector head of the invention useful in understanding the operation thereof.

As shown in FIG. 8(B), the invention overcomes this deficiency by maintaining tubing 16 in constant cross-section regardless of pressure variations in fluid in the tubing lumen. The light from light source 60 continues to be focused on light detector 61 and an optimum output signal is developed for maximum capability in distinguishing between fluid present and fluid absent conditions.

Figure 9:
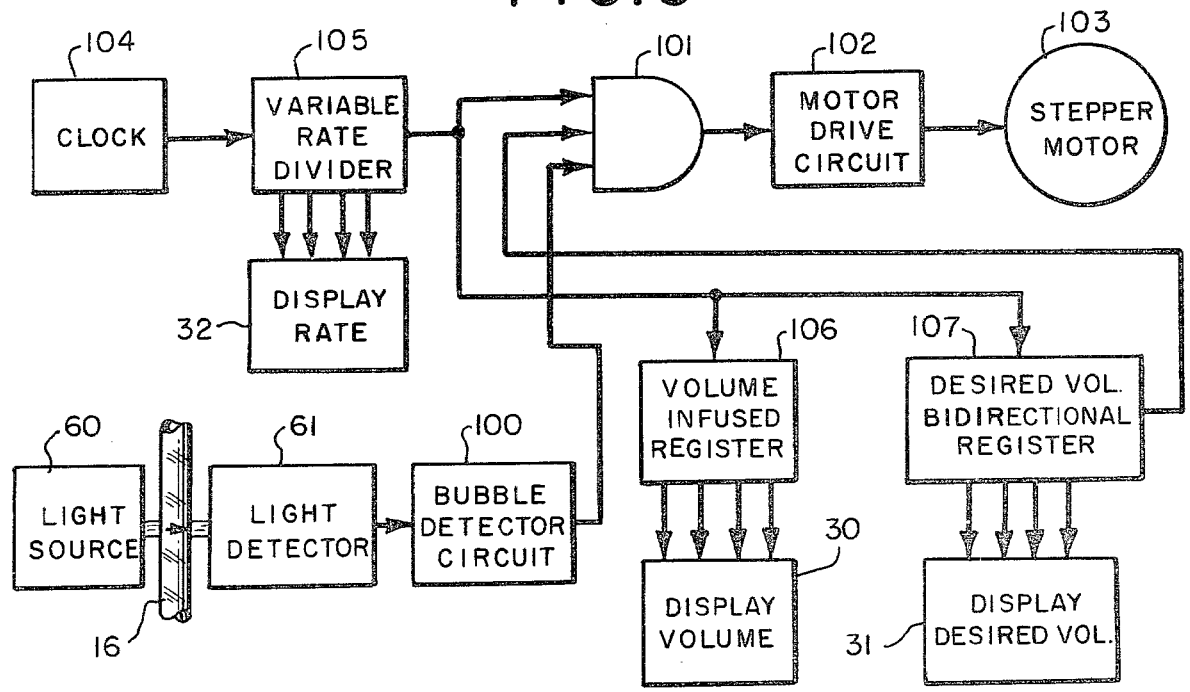
FIG. 9 is a simplified functional block diagram of the control system of the metering apparatus of FIG. 1.

The output of light detector 61 is applied to appropriate bubble detector circuitry wherein it is utilized to develop a control signal suitable for controlling the operation of the metering apparatus. Referring to FIG. 9, in the present embodiment the output of light detector 61 is applied to a bubble detector circuit 100 wherein a control signal is developed indicative of the presence or absence of fluid in tubing segment 16. This control signal is applied to one input of an AND gate 101, wherein it serves to control the application of control pulses to the motor drive circuit 102 of a stepper motor 103, which is utilized to drive the peristaltic rotor 40 of the apparatus.

Control pulses for drive circuit 102 are obtained from a pulse source in the form of a clock 104. The clock pulses are divided to a lower frequency by a variable-rate divider 105, and applied through AND gate 101 to the motor drive circuit. The division factor of rate divider 105 is selected by the operator to obtain a desired rate. The pulses derived from divider 105 are also applied to a volume register 106 wherein they are counted for use by volume display 30. The divided pulses are also applied to a bi-directional register 107 which supplies an inhibit signal to AND gate 101 upon the desired volume having been infused. The counting state of this register is displayed by display 31.

Referring to FIG. 10, a preferred bubble detector circuit 61 may comprise a multi-vibrator 111 consisting of three NAND gates 112, 113 and 114. A capacitor 115 connected to the output of gate 113 and a potentiometer 116 connected to the output of gate 114 provide an RC time constant which determines the frequency of the multi-vibrator output signal in a manner well known to the art. A diode 117 is connected between the arm of potentiometer 116 and the output of gate 114 to vary the duty cycle of the oscillator output signal. A fixed resistance 118 connected in series with the body of potentiometer 116 provides a desired adjustment range.

The AC signal generated by multi-vibrator 111 is applied through a resistance 119 and transistor 120 to light source 60. The AC signal developed by multi-vibrator 111 is amplified by transistor 120 and utilized to drive the LED, causing the LED to produce a light output which varies at a rate dependent on the output frequency of the multi-vibrator.

The alternating light developed by the LED is converted by phototransistor detector 122 to an output signal indicative of the strength of the transmitted light. The emitter of transistor 123 is connected to ground through a resistor 124, and is connected through respective diodes 125-127 to respective inputs of a threshold trigger device in the form of a dual Schmidt trigger 128. The cathodes of diodes 125-127 are connected to ground by respective parallel combinations of capacitors 130-132 and resistors 133-135. These elements serve in conjunction with the diodes as alternating current detectors, generating a DC signal at the inputs of trigger 128 dependent on the amplitude of the AC signal produced by detector 61. The dual Schmitt trigger 128, which may be a commercially available component such as the type NC14583B Schmitt trigger marketed by Motorola, Inc., of Schaumburg, Ill., produces an output upon reduction of either of its input signals falling below a predetermined threshold level. The input associated with diode 125 functions as an enabling input for both triggers. The outputs of Schmidt triggers 128, which comprise a first control signal, are applied to one input of a logic OR gate 129.

The emitter of transistor 123 is also connected to ground through series-connected resistors 136 and 137. The signal developed at the junction of these two resistors is filtered by a series-connected resistor 138 and a short-connected capacitor 139 and resistor 140 connected to ground. This forms a second control signal, which is applied to the remaining input of OR gate 129. In this way, OR gate 129 is provided with the output signal developed by the dual Schmitt trigger 128, and with the DC control signal developed across capacitor 139, either of which can result in an output from the gate in the event of the occurence of a bubble in tubing 16. The output of Schmitt triggers 128 and the output of OR gate 129 are also connected to the positive unidirectional current source of the system by respective resistors 143 and 144.

Since the output of OR gate 129 is dependent on both the amplitude of the AC signal as rectified and applied to the parallel-connected Schmitt triggers 128, and on the DC signal developed across capacitor 139, the bubble detector utilized in the metering apparatus provides two control channels. The first channel, which utilizes Schmitt triggers 128, establishes a highly precise threshold below which an alarm output is produced. The second channel, which depends only on the input characteristic of gate 129, serves to provide an alarm output in event of failure of resistor 124 in the photodetector bias circuit.

In order for bubble detector 62 to not provide an output, it is necessary that the DC signals applied to the Schmitt triggers as a result of rectification by diodes 126 and 127 be above a predetermined minimum level, which is possible only when there is fluid within tubing segment to provide a lens to direct light from light source 60 to light detector 61.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

We claim:

1. In a flow metering apparatus for controlling the flow of fluid through an administration set of the type having transparent tubing subject to deformation from internal fluid pressure, a bubble detector comprising, in combination:

a light source arranged at one side of the tubing;

a light detector generally arranged at the opposite side of the tubing opposite said light source and defining a light path through the tubing, said detector generating an output signal indicative of the intensity of light from said light source transmitted through the tubing, the intensity of said transmitted light being dependent on the presence of fluid within the lumen of the tubing and on the shape of the lumen between said source and said detector;

control circuit means responsive to said output signal for interrupting operation of the flow metering apparatus upon the intensity of said transmitted light falling below a predetermined minimum level; and platen means comprising a pair of forming members engaging said tubing from opposite sides thereof about a substantial portion of the circumference of the tubing adjacent said light path for preventing deformation of the tubing and consequent changes in the intensity of said transmitted light with fluid pressure changes in the lumen of the tubing, at least one of said forming members being mounted for movement in a direction generally perpendicular to the axis of the tubing so as to be disengageable from the tubing to facilitate insertion or removal of the tubing from said platen means.

2. A bubble detector as defined in claim 1 wherein the engaging surface of said forming member conforms generally to the non-expanded shape of said tubing.

3. A bubble detector as defined in claim 2 wherein said non-expanded shape of said tubing is cylindrical.

4. A bubble detector as defined in claim 1 wherein the tubing of the flow metering apparatus is formed of vinyl.

5. A flow system for infusing fluid from a reservoir into the human body, said system including, in combination:

a length of transparent tubing, said tubing being subject to deformation from internal fluid pressure;

metering means operatively engaging said tubing for urging fluid through said tubing at a predetermined rate;

a light source arranged at one side of said tubing downline of said metering means;

a light detector generally arranged at the opposite side of said tubing opposite said light source and defining a light path through said tubing, said detector generating an output signal in response to the intensity of light from said light source transmitted through said tubing, the intensity of said transmitted light being dependent on the presence of fluid within the lumen of said tubing and on the shape of the lumen between said source and said detector;

control circuit means responsive to said output signal for interrupting operation of said flow metering apparatus upon the intensity of said transmitted light falling below a predetermined minimum level; and platen means comprising a pair of forming members engaging said tubing from opposite sides thereof about a substantial portion of the circumference of said tubing adjacent said light path for preventing deformation of said tubing and consequent changes in the intensity of said transmitted light with fluid pressure changes in said lumen of said tubing, at least one of said forming members being mounted for movement in a direction generally perpendicular to the axis of said tubing so as to be disengageable from said tubing to facilitate insertion or removal of said tubing from said platen means.

6. A flow system as defined in claim 5 wherein the engaging surface of said forming member conforms generally to the non-expanded shape of said tubing.

7. A flow system as defined in claim 6 wherein said non-expanded shape of said tubing is cylindrical.

8. A flow system as defined in claim 5 wherein said tubing is formed of vinyl.

* * * * *